United States Patent [19]

Renheim

[11] 4,213,465
[45] Jul. 22, 1980

[54] ELECTROENCEPHALOGRAPH

[75] Inventor: Gunnar Renheim, Vällingby, Sweden

[73] Assignee: Siemens Aktiengesellschaft, Berlin & Munich, Fed. Rep. of Germany

[21] Appl. No.: 916,059

[22] Filed: Jun. 16, 1978

[30] Foreign Application Priority Data

Jun. 20, 1977 [DE] Fed. Rep. of Germany ....... 2727583

[51] Int. Cl.$^2$ .............................................. A61B 5/04
[52] U.S. Cl. ............................... 128/731; 346/33 ME
[58] Field of Search ............................... 128/731, 732; 346/33 ME

[56] References Cited

U.S. PATENT DOCUMENTS

| 3,696,808 | 10/1972 | Roy et al. | 128/731 |
| 4,037,586 | 7/1977 | Grichnik | 128/731 |
| 4,084,583 | 4/1978 | Hjort | 128/731 |

OTHER PUBLICATIONS

Siemens Brochure, "Mingograf EEG Universal".

Primary Examiner—Lee S. Cohen
Attorney, Agent, or Firm—Hill, Van Santen, Steadman, Chiara & Simpson

[57] ABSTRACT

A number of measuring electrodes for emplacement on the head of a patient, signal amplifiers whose input channels are connectable, via a selector, to the measuring electrodes according to a pattern selection program, and recorders controlled by the output signals of the signal amplifiers. The selector manifests, in a head-image area, one electrode switch for each measuring electrode, by means of which electrode switch the measuring electrode is connectable to an input channel, and which electrode switch is arranged in a position relative to the head-image area corresponding to the application location of the measuring electrode.

18 Claims, 5 Drawing Figures

ELECTROENCEPHALOGRAPH

BACKGROUND OF THE INVENTION

The invention relates to an electroencephalograph comprising a number of measuring electrodes for emplacement on the head of the patient, comprising signal amplifiers whose input channels are connectable to the measuring electrodes, via a selector means in accordance with a pattern selection program, and comprising recorders controlled by the output signals of the signal amplifiers.

Signals of the central nervous system are measured with an electroencephalograph. This measurement proceeds either by means of a number of measuring electrodes arranged on the cranium in accordance with an international standardization, or by means of a number of measuring electrodes which are applied on the exposed cerebral cortex or on the cerebral membrane (meninx). The electric activity of the nerve cells and of the surrounding medium is detected beneath the electrodes in the form of corresponding potential changes. An electroencephalograph of the type initially cited is known from the brochure "Mingograph EEG Universal" of the Siemens Corporation. Functioning as the selector means, selector wheels arranged in a row, are present which are individually manually rotatable for the adjustment of the pattern selection program. The known selector means is bulky, expensive, and complicated in construction. In addition, its operation is complicated and difficult to survey.

SUMMARY OF THE INVENTION

The object underlying the invention consists in producing an encephalograph of the type initially cited which is simplified as compared with the state of the art with regard to affording a clear overview and in the construction of the operating installation.

In accordance with the invention, this object is achieved by virtue of the fact that the selector means of the EEG-apparatus manifests, in a head-image area, one electrode switch for each measuring electrode, by means of which electrode switch the measuring electrode is connectable to the input channel, and which electrode switch is arranged in a position relative to the head-image area corresponding to the application location of the measuring electrode. In the case of the inventive electroencephalograph, a simple orientation of the user on the basis of the head-image is possible for the purpose of selecting the pattern selection program. In addition, the selector means may be simply and cheaply constructed with the use of standardized electronic modules.

Further advantages and details of the invention shall be apparent from the subclaims.

In the following, the invention shall be explained in greater detail on the basis of the sample embodiment illustrated in the accompanying sheets of drawings; and other objects, features and advantages will be apparent from this detailed disclosure and from the appended claims.

DETAILED DESCRIPTION

Figure 1:
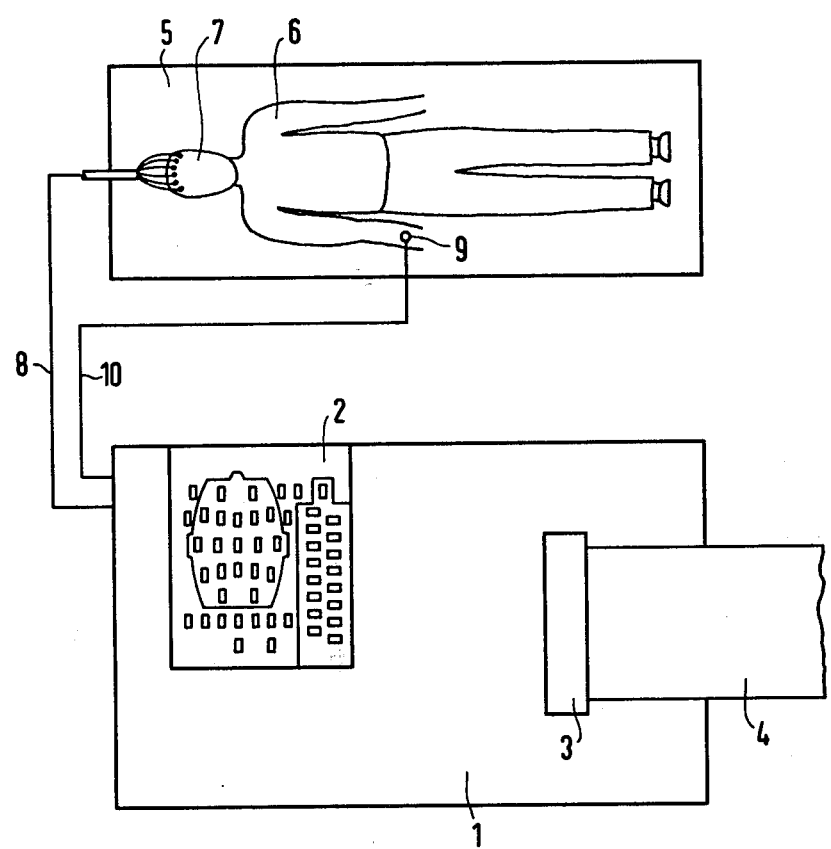
FIG. 1 illustrates a schematic representation of an electroencephalograph in accordance with the invention with a patient connected thereto.

FIG. 1 illustrates an electroencephalograph 1 with a selector means 2 and a support mounting 3 for e.g. sixteen non-visible recorders; for example, ink jet recorders according to the German Letters Patent No. 821,065, wherein a recording channel is associated with each recorder. The recorders are directed at a recording carrier 4, and there they record, in e.g. sixteen channels, the bio-electric brain activity. A patient 6 lying on a bed 5 is connected, by means of a number of measuring electrodes applied to his head 7, to the electroencephalograph 1 via a multiconductor cable 8. In addition, by means of a measuring electrode 9 applied on one arm, the patient 6 is connected, via a line 10, to the electroencephalograph for an EKG-recording. The electric activity of the nerve cells beneath the electrodes is converted in electroencephalograph 1 into corresponding signals with the aid of means which shall be described later, and said signals are then conveyed to the recorders.

Figure 2:
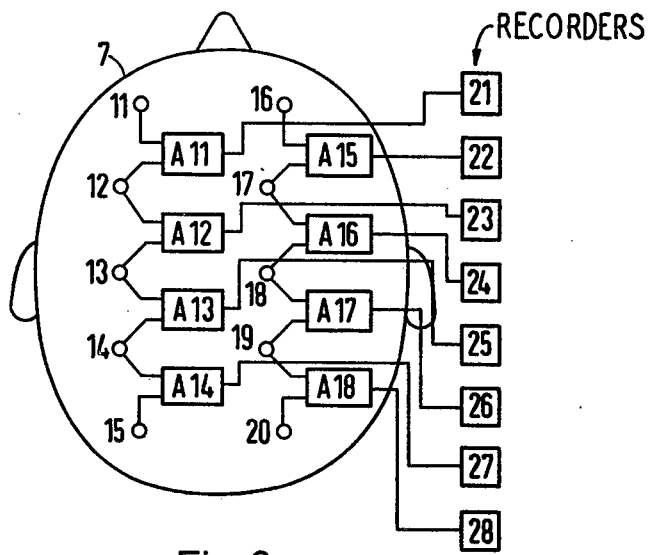
FIGS. 2 and 3 illustrate schematic representations for the purpose of explaining known measuring procedures.

The measuring methods may be divided into bipolar and unipolar measuring procedures. In the case of a bipolar measuring procedure, the differential voltages are delivered to signal amplifier inputs which are detected in pairs between the measuring electrodes. FIG. 2 explains a bipolar measuring procedure. Ten measuring electrodes 11 through 20 are placed on the head 7 of the patient. Potential differences prevailing between the respective measuring electrodes are conveyed in pairs to the amplifier inputs of the amplifiers A11 through A18 which are associated with the measuring electrodes 11 through 20. Subsequent to amplification, the differential voltages are delivered to recorders 21 through 28.

Figure 3:
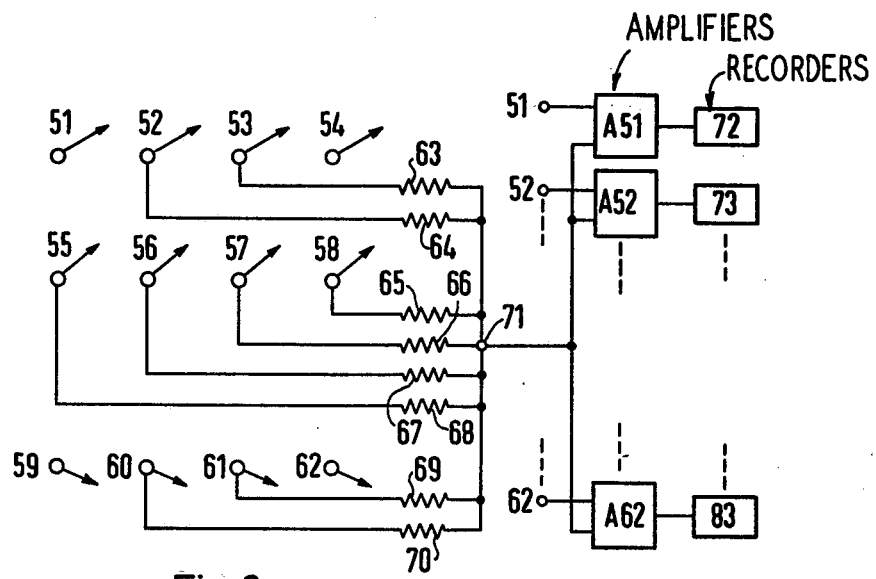

In the case of a unipolar measuring procedure, the differential voltages between a number of measuring electrodes and one reference point in each instance which is common to these measuring electrodes are detected. FIG. 3 illustrates such a unipolar measuring procedure wherein the reference point is the central point of a resistance star circuit which is connected via equal resistance values to all measuring electrodes (possibly with the exception of those measuring electrodes whose signals, as is known from experience, would falsify the measurement results because they are caused e.g. by muscular activity). Here there are twelve measuring electrodes 51 through 62 present which are each connected to an input of amplifiers A51 through A62. There are connected to eight measuring electrodes 52, 53, 55, 56, 57, 58, 60, 61, resistances 63 through 70 of equal magnitude whose one ends are combined into a common circuit point 71 (reference point). All twelve amplifiers A51 through A62 are connected to point 71 at their second inputs. Of the four measuring electrodes 51, 54, 59 and 62, it is assumed that they, more than the remaining measuring electrodes, detect potentials of a non-cerebral nature; for example, potentials caused by muscular activity, and they are therefore not connected to the resistance star circuit. Each of the amplifiers A51 through A62 measures the difference between a respective individual electrode potential and an average (or mean) potential. The differential voltages are delivered to recorders 72 through 83 for the purpose of recording.

Figure 4:
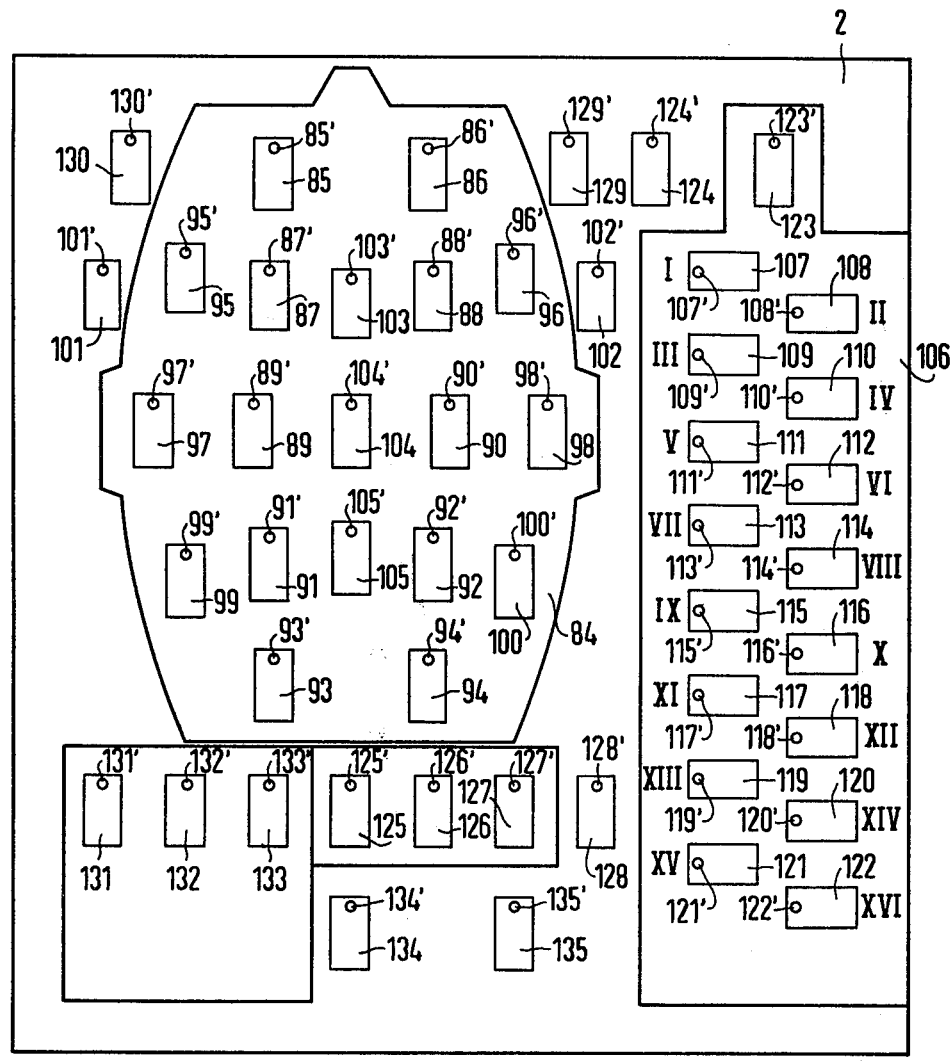
FIG. 4 illustrates the selector means in the case of the electroencephalograph according to FIG. 1.

The selector means 2 of electroencephalograph 1 manifests, according to FIG. 4, in association with a head image 84, one finger-actuatable electrode switch 85 through 105 for each measuring electrode on the head 7 of patient 6, through which switch the measuring electrode is connectable to an input channel of a signal amplifier described later, and which switch is arranged in a position relative to head image 84 corresponding to the application location of the associated measuring electrode. Outside the head image 84, but in association therewith, there are arranged electrode switches 101 and 102 which are associated with measuring electrodes applied in the region of the ears of patient 6.

Figure 5:
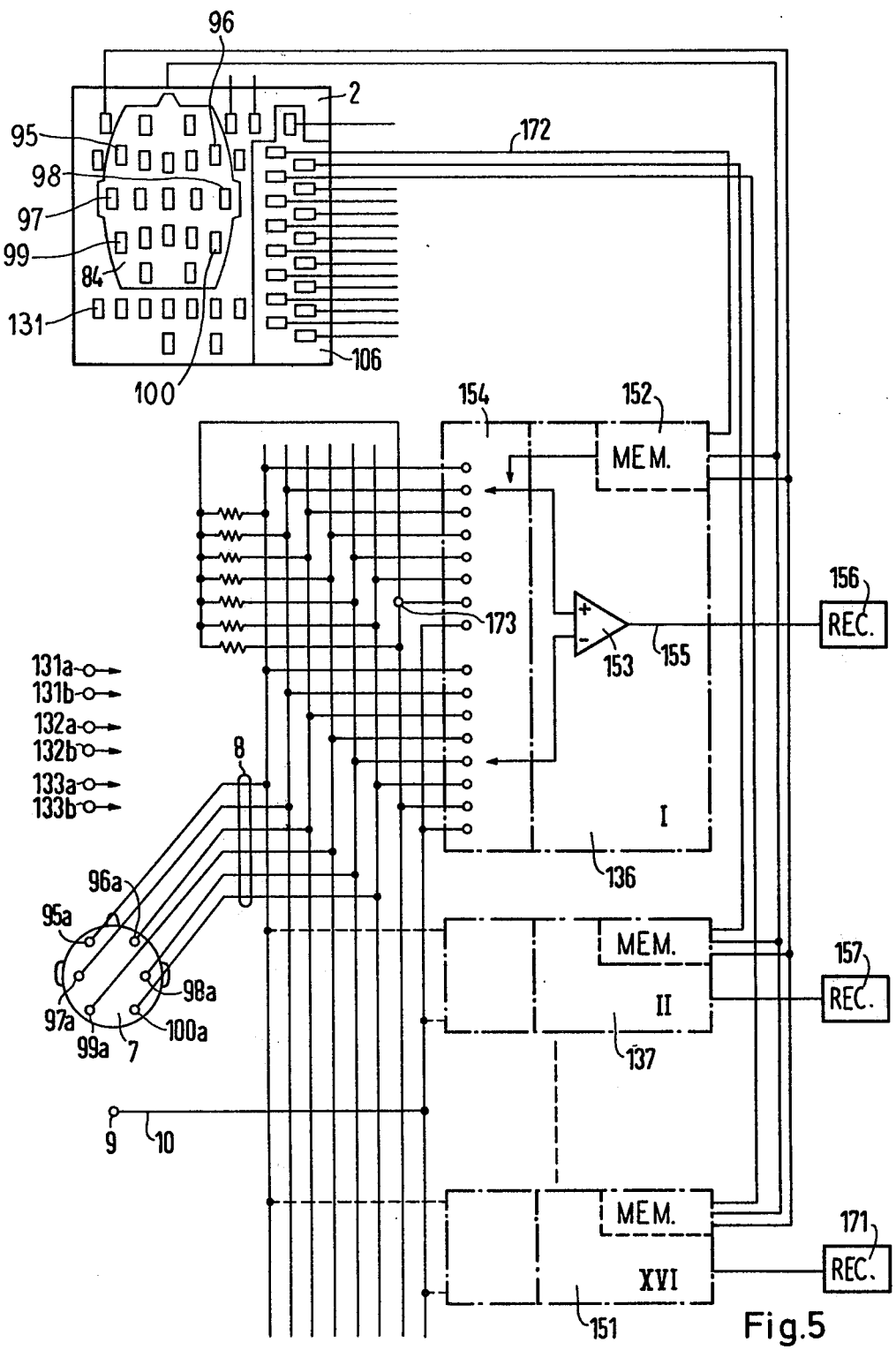
FIG. 5 illustrates a selection circuit for the selector means according to FIG. 4.

The switches 125 through 128, connected to channel blocks 136 through 151, FIG. 5, are likewise electrode switches with which is associated one individual measuring electrode each which can be randomly secured to the head 7 of patient 6. The selector means 2, in addition, has a channel selector for the input channels of the signal amplifiers. The channel selector manifests a number of finger-actuatable channel switches 107 through 122, said number corresponding to the number of recording channels of the electroencephalograph 1, and which channel switches are arranged in a switching field 106 which is adjacent the head image 84. There is associated with each electrode switch 85 through 105, and with each channel switch 107 through 122, an indicator lamp 85′ through 105′, or 107′ through 122′, respectively, said indicator lamp being connected to a selector circuit represented in FIG. 5, and which indicator lamp lights up when the associated electrode switch or channel switch is actuated, respectively. The selection circuit is constructed such that, of the indicator lamps of two successively actuated electrode switches, the one lights up with a constant brightness and the other blinks. In the sample embodiment, the indicator lamp of that particular electrode switch which connects a measuring electrode to a minus input of a signal amplifier lights up with constant light intensity, and the display lamp of that particular electrode switch which connects a measuring electrode to a plus input of a signal amplifier blinks.

Electrode switches 85 through 105 and channel switches 107 through 122 are interconnected with the inputs of the signal amplifiers via the selection circuit illustrated in FIG. 5 and described later, such that, subsequent to the selection of a recording channel via the channel selector 106, those particular measuring electrodes are connected to the inputs of the selected signal amplifier which correspond to the actuated electrode switches.

The functions of switches 123, 124, 129, 130, 131 through 133, as well as of switches 134 and 135 in FIG. 4, shall be explained in greater detail later.

FIG. 5 illustrates the selection circuit of the selector means 2. The selector means 2 is connected to the head 7 of patient 6 via sixteen channel blocks, of which only channel blocks 136, 137, 151, are illustrated in FIG. 5, and via twenty-one measuring electrodes, of which only six measuring electrodes 95a through 100a are illustrated. Each channel block (for example, 136) manifests a memory (for example, 152) for storing the information which has been programmed via the selector means 2, a signal amplifier (for example, 153), and a scanner or selector switch means 154 controllable by means of the memory (for example, 152), for the purpose of selecting from the available input signals those of desired measuring electrodes. The signals of the selected measuring electrodes are conveyed to the signal amplifiers (for example, 153). The output signals of the signal amplifiers 153, for example, are delivered via a connection line 155 to a recorder (for example, 156) for recording. Each channel block is associated with one recorder 156 through 171 each.

If patient 6 is to be measured according to a bipolar method illustrated in FIG. 2, the output signal in each recording channel is formed by two measuring electrodes in each instance. If e.g. the potential between the measuring electrodes 95a and 97a is to be formed on the recording channel I, channel switch 107, associated with channel I, is first actuated until its indicator lamp 107′ is energized. This information is delivered via the connection line 172 to the memory 152. Then the electrode switch 95, present within the head-image area 84 of the selector means 2, is actuated whereby its indicator lamp 95′ is energized to produce a constant light intensity. Memory 152 now controls scanner 154 such that the signal of measuring electrode 95a is conveyed to the minus input of signal amplifier 153. Thereafter, the electrode switch 97 is actuated, whereby its indicator lamp 97′ blinks. The memory 152 now controls scanner 154 such that the signal of measuring electrode 97a is conveyed to the plus input of the signal amplifier 153.

The selection circuit of FIG. 5 is constructed such that, pursuant to a successive actuation of two electrode switches, the minus input of the signal amplifier of the selected input channel is seized in response to actuation of a first actuated electrode switch, and the plus input of said signal amplifier is seized in response to actuation of a second actuated electrode switch. The polarity of the inputs is thus determined by the sequence of actuation of the electrode switches. Thus, for each recording channel I through XVI, the potential between two selected electrodes applied on the head 7 can be supplied to the associated differential amplifier.

When one of the channel switches 107 through 122 is actuated, indicator lamp 130′ of switch 130 is energized to produce a constant light intensity. This signifies that the initially actuated electrode switch connects one measuring electrode for a differential signal to be formed by two measuring electrodes, said one connected measuring electrode leading to the minus input of the selected signal amplifier. Subsequent to actuation of the first electrode switch, indicator lamp 130′ blinks. This signifies that the electrode switch actuated in the second instance connects a measuring electrode which leads to the plus input of the selected signal amplifier. Switch 130, in addition, is a cancel switch, which acts upon channel blocks 136 through 151 in such a manner that the electrode pair which has been programmed-in last is cancelled in the memory, in order that, instead of this electrode pair, a new randomly selected electrode pair can be programmed-in.

Upon actuation of one of switches 131 through 133 of the selector means 2, a differential connection is formed between two measuring electrodes (131a, 131b; 132a, 132b; 133a, 133b) in each instance, which are fixedly associated with the switches 131 through 133, and the resultant differential signal can be delivered via channel switches 107 through 122 to any of the recording channels I through XVI. There are associated with these additional electrode pairs fixed polarities which can only be reversed in polarity if the electrodes on head 7 exchange their places. The indicator lamps 131' through 133', upon actuation of switches 131 through 133, always are energized to produce a constant light intensity.

If the patient 6 is to be measured according to a unipolar method, differential voltages are detected between a number of measuring electrodes and one reference point in each instance which is common to these measuring electrodes. In order to rapidly connect such a reference point, for example to all minus inputs of the signal amplifiers, switch 123 is actuated. The desired reference point can now be selected by means of the electrode switches 85 through 105 on the head-image 84. Subsequently, upon actuation of the channel switches and the electrode switches, the signals of the selected measuring electrodes are conveyed to the second inputs of the signal amplifiers.

If the bioelectric activity of patient 6 is to be measured in accordance with a further unipolar method illustrated in FIG. 3, wherein the reference point is the central point of a resistance star circuit, the desired recording channels are first selected with channel switches 107 through 122. Switch 134 is then actuated, such that the signal of the neutral point 173 in FIG. 5 (71 in FIG. 3) is delivered to the one input of each signal amplifier selected by means of the channel switches. To this end, switch 134 is connected to all channel blocks 136 through 151. The neutral point 173 can now form a differential connection with any of the measuring electrodes, the neutral point being established independent of which of electrode switches 85 through 105 and 125 through 128 may be subsequently actuated. If it is desirable to carry out, on a recording channel, an EKG-recording, the channel key corresponding to the desired recording channel is actuated, and subsequently, the key 135, likewise connected to the channel blocks 136 through 151, is actuated (or touched), whereby the scanner associated with this recording channel locates (or seeks out) the signal input of the EKG-electrode and connects the latter with the signal amplifier. The indicator lamp 135', upon actuation of switch 135, is always energized to produce a constant light intensity.

Upon reprogramming one of the recording channels I through XVI which was previously programmed with the switches 131 through 133 with measuring electrodes assigned to fixed polarities, or with the EKG-switch 135, it is necessary that a measuring electrode be selected for the minus—as well as for the plus—input of the corresponding signal amplifier. After a desired recording channel has been selected with one of channel switches 107 through 122, that particular measuring electrode which is to be delivered to the minus input of the signal amplifier is selected. If the corresponding electrode switch is actuated, its indicator lamp blinks, and the indicator lamp of the particular switch which belongs to one of the not yet cancelled electrode signals programmed by means of switches 131 through 133 and 135, blinks with a frequency which is substantially greater than the conventional blinking frequency of an indicator lamp of an electrode switch which seizes a minus input of a signal amplifier. This is a warning or reminder signal which shows that the programming is not terminated. If the desired second electrode switch of the electrode pair is switched on, the warning signal is cancelled.

There is present on selector means 2 a test or check switch 124, upon actuation of which the indicator lamps of the electrode switches and the indicator lamps of the channel switches are automatically controllable with the object of a channel-wise sequential display of the existing pattern selection program. A selected program can thereby be reviewed by the user. In addition, a memory key 129 is present on the pattern selector 2 which is provided for the storage of a selected program. The switches cited in the specification are key switches, for example, of the sensor-type responsive to momentary actuation to actuate a latch circuit in the associated or activated memory.

The indicator lamps 85' through 105', 107' through 122' are likewise controlled via conductors such as illustrated in FIG. 5 connected to the channel blocks 136 through 151, and are actuated by the memories 152, etc., of the channel blocks 136 through 151 for the purpose of emission (or release) of the described light signals.

Electrode pairs 131a, 131b; 132a, 132b; 133a, 133b, are associated with switches 131 through 133, and these electrode pairs, in accordance with the wish of the user, may be applied on the head 7 of the patient. The electrodes 131a through 133b are likewise connected to all channel blocks 136 through 151, and they are capable of connection to a selected channel block by means of switches 131 through 133. The control of the indicator lamps 131' through 133' likewise proceeds from channel blocks 136 through 151 via conductors such as illustrated in FIG. 5.

The channel blocks 136 through 151 also control the additional indicator lamps 124' through 135' in the manner described.

It is also possible to provide as the selection circuit a ciruit in accordance with the third figure of the U.S. Pat. No. 4,037,586, wherein the reference numbers fifteen and twenty-one of this figure correspond to the selector means 2 of the present application.

It will be apparent that many modifications and variations may be effected without departing from the scope of the novel concepts and teachings of the present invention.

I claim as my invention:

1. An electroencephalograph comprising a number of measuring electrodes for emplacement on the head of the patient, signal amplifiers whose input channels are connectable to the measuring electrodes, selector means for connecting the measuring electrodes to the input channels in accordance with a pattern selection program, and recorders connected with the respective signal amplifiers and controlled by the output signals of the signal amplifiers, characterized in the selector means (2) having a head-image area (84), and having one manually operable electrode switch (e.g. 95–100, FIG. 5) for each measuring electrode (e.g. 95a–100a, FIG. 5), said selector means having selection circuit means (e.g. 152, 154) connected with said manually operable electrode switches (e.g. 95–100) and with said measuring electrodes (e.g. 95a–100a) and operable for selectively connecting said measuring electrodes with respective ones of said input channels in accordance with the pattern of actuation of said manually operable electrode switches, such that the respective measuring electrode (e.g. 95a–100a, FIG. 5) corresponding to each actuated electrode switch is connected to a respective input channel, and said electrode switches being arranged in positions relative to the head-image area (84) corresponding to the application locations of the respective measuring electrodes (e.g. 95a–100a, FIG. 5).

2. An electroencephalograph according to claim 1, with said selection circuit means comprising a selection circuit (e.g. 152, 154) associated with each respective input channel, the selection circuits (e.g. 152, 154) associated with the respective input channels (I through XVI) being each connected with said manually operable electrode switches and with said measuring electrodes and being each operable for selectively connecting said measuring electrodes with the associated input channel in accordance with the one of said electrode switches which is actuated during a selection operation with respect to such selection circuit, said selector means (2) having a manually operable channel selector (106) connected with said selection circuits for selectively enabling a selection operation by any selected one of said selection circuits such that the actuation of any of the electrode switches effects the interconnection of the respective associated measuring electrode with the input channel associated with the selected selection circuit.

3. An electroencephalograph according to claim 2, characterized in that the channel selector (106) manifests a number of finger-actuatable channel switches (107 through 122), said number corresponding to the number of input channels, which channel switches are arranged in a switching field (106) which is adjacent the head-image area (84).

4. An electroencephalograph according to claim 3, characterized in that the channel switches (107 through 122) are key switches.

5. An electroencephalograph according to claim 2 with an electrode switch indicator lamp (85' through 105') associated with each electrode switch and connected with said selection circuit means for lighting up when the associated electrode switch is actuated, channel selector indicator lamps (107' through 122') connected with said selection circuits so as to light up when the channel selector (106) is operated to select the associated one of said selection circuits, and indicator lamp means comprising the electrode switch indicator lamps and the channel selector indicator lamps and being controllable for displaying the pattern of actuation of said electrode switches and said channel selector, and means comprising a manually actuatable test switch (124) connected with said selection circuit means and with said indicator lamp means and actuatable for energizing said indicator lamp means to display the pattern selection program selected by said electrode switches and said channel selector.

6. An electroencephalograph according to claim 1, characterized in that the electrode switches (85 through 105) are key switches.

7. An electroencephalograph according to claim 1, characterized in that there is associated with each electrode switch (85 through 105) an indicator lamp (85' through 105'), connected to the selector means (2) which lights up when the associated electrode switch (85 through 105) is actuated.

8. An electroencephalograph according to claim 7, characterized in that the selector means (2) has means such that the indicator lamps (85' through 105') of two electrode switches (85 through 105) which are successively actuated during a selection operation respectively provide different types of light emission.

9. An electroencephalograph according to claim 8, characterized in that the selector means has a selection circuit (FIG. 5) with means such that, of the indicator lamps (85' through 105') of two successively actuated electrode switches (85 through 105), the one is energized to provide a constant light intensity and the other blinks.

10. An electroencephalograph according to claim 7 with indicator lamp means comprising the indicator lamps (85' through 105') associated with said electrode switches being controllable for displaying the pattern of actuation of said electrode switches (85 through 105), and means comprising a manually actuatable test switch (124) connected with said selection circuit means and with said indicator lamp means and actuatable for energizing said indicator lamp means to display the pattern selection program selected by said selector means.

11. An electroencephalograph according to claim 1 with said selector means (2) having manually actuatable channel selector means (123) connected with said selection circuit means and operable for enabling a selection operation with respect to all of said input channels such that a single actuation of one of said electrode switches effects the interconnection of the respective associated measuring electrode with all of the input channels.

12. An electroencephalograph according to claim 1 with said selection circuit means comprising a memory (152) connected with said electrode switches for the storage of the pattern selection program selected thereby, and means comprising a memory key (129) connected with said memory for controlling the storage of a selected pattern selection program in said memory.

13. An electroencephalograph according to claim 1, with said signal amplifiers comprising differential amplifiers having respective inputs, and said selection circuit means (FIG. 5) being constructed such that, pursuant to successive actuation of two electrode switches (85 through 105) the one input of the signal amplifier (153) of an input channel is seized according to actuation of a first electrode switch (85 through 105), and that the other input of said signal amplifier (153) of the input channel is seized according to the actuation of a second electrode switch (85 through 105), whereby the respective electrode which are connected to the respective inputs of each differential amplifier is fixedly determined by the sequence of actuation of the electrode switches (85 through 105).

14. An electroencephalograph according to claim 13, with said selection circuit means comprising memory means (152, etc.) connected with said selector means for storing information in accordance with a pattern of actuation of said manually operable electrode switches, and means comprising a cancellation switch (13) connected with said selection circuit means such that actuation of the cancellation switch cancels the information in said memory means produced by the successive action of two electrode switches which were actuated with respect to the most recently programmed input channel.

15. An electroencephalograph according to claim 13, with signal lamp means comprising a signal lamp (130') having different modes of energization and means responsive to the actuation of the first of two electrode switches during programming of an input channel to change the mode of energization of said signal lamp (130') so that the signal lamp, during programming of an input channel, displays respective light signals indicating whether or not the first of two electrode switches has been actuated, and thus indicates to which input of the differential amplifier of the input channel being programmed the next selected electrode will be connected.

16. An electroencephalograph according to claim 1, characterized in that a number of additional electrodes is present (131a through 133b, etc.), which can be freely placed on the head (7) of a patient, and means comprising additional electrode switches (131 through 133) arranged outside the head-image area (84) and connected with said selection circuit means for the purpose of connecting said additional electrodes to the input channels.

17. An electroencephalograph according to claim 1, characterized in that a neutral reference selector switch (134) is provided outside the head-image area (84), and means comprising said neutral reference selector switch (134) connected with said selection circuit means for the purpose of connecting a neutral reference point (173) to predetermined input channels.

18. An electroencephalograph according to claim 1, characterized in that an EKG-electrode is provided, an EKG-electrode selector switch being outside the head-image area (84), and means comprising said EKG-electrode selector switch connected with said selection circuit means for the purpose of connecting the EKG-electrode (9) to an input channel.

* * * * *